US010311373B2

(12) United States Patent
Rapaka et al.

(10) Patent No.: US 10,311,373 B2
(45) Date of Patent: Jun. 4, 2019

(54) SUBJECT-SPECIFIC ASSESSMENT OF NEUROLOGICAL DISORDERS WITH BIOCHEMICAL PROPAGATION MECHANISMS

(71) Applicant: Siemens Healthcare GmbH, Erlangen (DE)

(72) Inventors: Saikiran Rapaka, Pennington, NJ (US); Hasan Ertan Cetingul, Fulton, MD (US); Francisco Pereira, Jersey City, NJ (US); Dorin Comaniciu, Princeton Junction, NJ (US); Alma Gregory Sorensen, Charlestown, MA (US)

(73) Assignee: Siemens Healthcare GmbH, Erlangen (DE)

( * ) Notice: Subject to any disclaimer, the term of this patent is extended or adjusted under 35 U.S.C. 154(b) by 716 days.

(21) Appl. No.: 14/688,148

(22) Filed: Apr. 16, 2015

(65) Prior Publication Data

US 2016/0306942 A1    Oct. 20, 2016

(51) Int. Cl.
| | |
|---|---|
| *G06N 20/00* | (2019.01) |
| *A61B 5/0476* | (2006.01) |
| *G16H 50/50* | (2018.01) |
| *A61B 5/055* | (2006.01) |
| *A61B 5/00* | (2006.01) |

(52) U.S. Cl.
CPC ........... *G06N 20/00* (2019.01); *A61B 5/0042* (2013.01); *A61B 5/0476* (2013.01); *A61B 5/055* (2013.01); *G16H 50/50* (2018.01); *A61B 5/4094* (2013.01); *A61B 5/72* (2013.01); *A61B 5/7264* (2013.01); *A61B 5/7278* (2013.01); *A61B 2576/026* (2013.01)

(58) Field of Classification Search
None
See application file for complete search history.

(56) References Cited

U.S. PATENT DOCUMENTS

2014/0024071 A1    1/2014 Kumar

FOREIGN PATENT DOCUMENTS

| CN | 104207775 A | 12/2014 |
|---|---|---|
| WO | WO2014025624 A1 | 2/2014 |

OTHER PUBLICATIONS

Brodbeck, Verena, et al. "Electrical source imaging for presurgical focus localization in epilepsy patients with normal MRI." Epilepsia 51.4 (2010): 583-591.*
Le Bihan, Denis, et al. "Diffusion tensor imaging: concepts and applications." Journal of Magnetic Resonance Imaging: An Official Journal of the International Society for Magnetic Resonance in Medicine 13.4 (2001): 534-546.*
Hadjikhani, Nouchine, et al. "Mechanisms of migraine aura revealed by functional MRI in human visual cortex." Proceedings of the National Academy of Sciences 98.8 (2001): 4687-4692.*
Dahlem, Markus A et al.:"Cortical hot spots and labyrinths: why cortical neuromodulation for episodic migraine with aura should be personalized"; in: Frontiers in computational neuroscience; Mar. 15, 2015.
Miura R.M. et al.:"Cortical spreading depression: An enigma"; in: The European Physical Journal. Special Topics, Springer Verlag; vol. 147; No. 1; pp. 287-302; Aug. 1, 2007.
Jeong, Won-Ki et al.:"Interactive Visualization of Volumetric White Matter Connectivity in DT-MRI Using a Parallel-Hardware Hamilton-Jacobi Solver"; in: IEEE Transactions on Visualization and Computer Graphics, IEEE Service Center, Los Alamitos, CA, US; vol. 13; No. 6; pp. 1480-1487; Nov. 1, 2007.
Hagmann, Patric et al.:"Mapping the Structural Core of Human Cerebral Cortex"; in: Physical Review Letters; (Daten wie vom EPA im European search report geliefert: vol. 87; No. 7; pp. 198701); Daten wie im Document enthalten: vol. 6 No. 7; pp. 1479-1493; Jan. 1, 2008.
Bojak, I. et al.:"Towards a model-based 1-7,9-H integration of co-registered electroencephalography / functional magnetic resonance imaging data with realistic neural population meshes"; in: Royal Society of London. Philosophical Transactions. Mathematical, Physical and Engineering Sciences; vol. 369; No., pp. 3785-3801, 2011.
Chinese Office Action dated May 14, 2018 in corresponding Chinese Patent Application No. 201610352607.5.
Audigier, Chloe; et al; "Lattice Boltzmann Method for Fast Patient-Specific Simulation of Liver Tumor Ablation from CT Images"; in MICCAI 2013, Part III, LNCS 8151; pp. 323-330, 2013. c Springer-Verlag Berlin Heidelberg 2013; K. Mod et al. (Eds.)).
Cetingul, H.E., et al.,"Group action induced averaging for HARDI processing" ISBI, pp. 1389-1392, 2012.
Cetingül, H. E., Afsari, B., & Vidal, R. (May 2012). An algebraic solution to rotation recovery in hardi from correspondences of orientation distribution functions. In Biomedical Imaging (ISBI), 2012 9th IEEE International Symposium on (pp. 38-41). IEEE.
Cetingul, H. E., et al. "Simultaneous ODF estimation and robust probabilistic tractography from HARDI." MICCAI Computational Diffusion MRI Workshop at MICCAI (2012).
Çetingül, H. E., Wright, M. J., Thompson, P. M., & Vidal, R. (2014). Segmentation of high angular resolution diffusion MRI using sparse Riemannian manifold clustering. IEEE transactions on medical imaging, 33(2), 301-317.
Çetingül, H. E., Dumont, L., Nadar, M. S., Thompson, P. M., Sapiro, G., & Lenglet, C. (Jun. 2013). Importance Sampling Spherical Harmonics to Improve Probabilistic Tractography. In Pattern Recognition in Neuroimaging (PRNI), 2013 International Workshop on (pp. 46-49). IEEE.

(Continued)

*Primary Examiner* — G Steven Vanni

(57) ABSTRACT

A method for subject-specific assessment of neurological disorders, the method includes receiving 3D image data representative of a subject's brain and identifying subject-specific anatomical structures in the 3D image data. A subject-specific model for electrical dynamics is created based on the 3D image data and the subject-specific anatomical structures and one or more functional indicators of neurological disorder are computed using the subject-specific model for electrical dynamics.

19 Claims, 4 Drawing Sheets

(56) References Cited

OTHER PUBLICATIONS

Dahlem, M.A., (2013) Models of cortical spreading depression, Scholarpedia.org, 2013.

Ding, L., Wilke, C., Xu, B., Xu, X., van Drongelene, W., Kohrman, M., & He, B. (2007). EEG source imaging: correlate source locations and extents with ECoG and surgical resections in epilepsy patients. Journal of clinical neurophysiology: official publication of the American Electroencephalographic Society, 24(2), 130.

Dreier, J. P. (2011). The role of spreading depression, spreading depolarization and spreading ischemia in neurological disease. Nature medicine, 17(4), 439.

Itu, L., Sharma, P., Mihalef, V., Kamen, A., Suciu, C., & Comaniciu, D. (May 2012). A patient-specific reduced-order model for coronary circulation. In Biomedical Imaging (ISBI), 2012 9th IEEE International Symposium on (pp. 832-835) IEEE.

Lakhan, S. E., Avramut, M., & Tepper, S. J. (2013). Structural and functional neuroimaging in migraine: insights from 3 decades of research. Headache: The Journal of Head and Face Pain, 53(1), 46-66.

Lipton, R. B., & Pearlman, S. H. (2010). Transcranial magnetic simulation in the treatment of migraine. Neurotherapeutics, 7(2), 204-212.

Pereira, Francisco, et al. "Creating group-level functionally-defined atlases for diagnostic classification." Pattern Recognition in Neuroimaging (PRNI), 2013 International Workshop on. IEEE, 2013.

J.W. Bohland et al., "Network, Anatomical, and Non-Imaging Measures for the Prediction of ADHD Diagnosis in Individual Subjects", Front. Syst. Neurosci. 2012, 6:78.

Rapaka, S., Mansi, T., Georgescu, B., Pop, M., Wright, G. A., Kamen, A., & Comaniciu, D. (Oct. 2012). LBM-EP: Lattice-Boltzmann method for fast cardiac electrophysiology simulation from 3D images. In International Conference on Medical Image Computing and Computer-Assisted Intervention (pp. 33-40). Springer, Berlin, Heidelberg.

Van Drongelen, Wim, et al. "Emergent epileptiform activity in neural networks with weak excitatory synapses." IEEE Transactions on Neural Systems and Rehabilitation Engineering 13.2 (2005): 236-241.

\* cited by examiner

SUBJECT-SPECIFIC ASSESSMENT OF NEUROLOGICAL DISORDERS WITH BIOCHEMICAL PROPAGATION MECHANISMS

TECHNICAL FIELD

The present invention relates generally to methods, systems, and apparatuses for performing an assessment of neurological disorder using imaging data and a patent-specific modeling process. The disclosed methods, systems, and apparatuses may be applied to, for example, imaging modalities such as Magnetic Resonance Imaging (MRI).

BACKGROUND

Mathematical models have been proposed for some neurological disorders characterized by a propagating process across the brain, of which one example is Cortical Spreading Depression (CSD). CSD is a massive but temporary perturbation in the cortical ionic homeostasis leading to a depression of neuronal activity that spreads through the cortex and the other gray matter regions in the brain. CSD has been suggested to be associated with migraines with aura, traumatic brain injury, epilepsy, ischemic stroke and subarachnoid hemorrhage. Another such disorder is epilepsy, in which many neurons may fire simultaneously, in a propagating wave originating at a focus. Medical imaging with different modalities (MRI, fMRI, dMRI, SPECT, PET, etc.) has been extremely helpful in understanding the effects in brain structure of neurological disorders. However, there has been less progress in understanding the functional characteristics of disorders where such propagating processes play a role, in a subject-specific manner. Doing this requires understanding how the propagating process moves across the surface of the cerebral cortex, and also taking into account the local and long-range connections between brain regions. Furthermore, there might also be additional measurements of other relevant aspects of function, such as external (EEG) or internal (ECoG) electrical activity, as the propagating process takes place.

Mathematically, the process of CSD has been modeled as a system of coupled reaction-diffusion equations for the different ions ($K^+$, $Ca^{2+}$, etc.), incorporating the physics of diffusion of ions in the extracellular space, along with the ionic dynamics controlled with additional gating variables. Computational models employing these equations have been used to explain the dynamics of the solitary wave, along with more complex features like the formation of spiral waves. However, very limited research has been done on real subject anatomies owing to multiple difficulties including lack of access to detailed cortical geometries; difficulty of modeling the dynamics over these complex geometric surfaces; and large computational demands of the numerical solver. Accordingly, it is desirable to produce a subject-specific model that provides accurate modeling of CSD (or other neurological disorders), while limiting the computational demand of the model's processing.

SUMMARY

Embodiments of the present invention address and overcome one or more of the above shortcomings and drawbacks, by providing methods, systems, and apparatuses that perform an assessment of neurological disorders using imaging data and a patent-specific modeling process. This technology is particularly well-suited for, but by no means limited to, imaging modalities such as Magnetic Resonance Imaging (MRI).

According to the some embodiments, a method for subject-specific assessment of neurological disorders, the method includes receiving 3D image data representative of a subject's brain and identifying subject-specific anatomical structures in the 3D image data. The subject-specific anatomical structures may be identified, for example, by applying a machine learning process to segment the subject's brain into a plurality of brain segments, which then are used as the anatomical structures. Once the structures have been identified, they are used, along with the 3D image data to create a subject-specific model for electrical dynamics (e.g., based on Lattice Boltzmann methods). One or more functional indicators of neurological disorder may then be computed using this model.

In some embodiments, diffusion data such as water may be used in conjunction with the model in the aforementioned method. For example, in one embodiment, diffusion data representative of diffusion of fluid through the subject's brain is identified in the 3D image data. Anatomical connections in the subject's brain may then be determined using the diffusion data. The subject-specific anatomical structures discussed above may then further comprise these anatomical connections.

In some embodiments of the aforementioned method, the 3D image data is used to perform surface based analysis of the subject's brain, yielding a flattened representation of the subject's brain. For example, in one embodiment, a surface mesh of the subject's brain is generated. This mesh is inflated and a flattening process is applied to yield the flattened representation of the subject's brain. Once the flattened representation is generated, a grid may be imposed on it using the subject-specific anatomical structures. The model may then be created using the grid.

In some embodiments, electrical sensing data representative of the subject's brain is used in creating the subject-specific model for electrical dynamics. For example, in one embodiment, an initial version of the subject-specific model for electrical dynamics is created based on the 3D image data and the subject-specific anatomical structures. This initial version is then refined using the electrical sensing data to yield the subject-specific model for electrical dynamics. The electrical sensing data may be received, for example, from an electroencephalography (EEG) or an electrocorticography (ECoG) device.

According to other embodiments, a method for subject-specific assessment of neurological disorders includes receiving 3D image data representative of a subject's brain and identifying subject-specific anatomical structures in the 3D image data. In some embodiments, these anatomical structures include the brain segments and anatomical connections identified using diffusion data. Once the anatomical structures are identified, a grid is then applied to the 3D image data using the structures and, in turn, a subject-specific model for electrical dynamics is generated using the grid. The grid is divided into blocks and a parallel computing platform is used to compute one or more functional indicators of neurological disorder by executing multiple copies of the subject-specific model for electrical dynamics in parallel. Each respective copy that is executed corresponds to one of the plurality of blocks. In some embodiments of this method, prior to execution, an electrical sensing data representative of the subject's brain may be used to refine the model.

According to other embodiments, a system for subject-specific assessment of neurological disorders includes an imaging device (e.g., MRI device) and a modeling computing system. The imaging device is configured to acquire 3D image data representative of a subject's brain. The modeling computing system is operably coupled to the imaging device and configured to use a plurality of components to simulate electrical dynamics across the subject's brain. These components may include a segmentation component configured to identify subject-specific anatomical structures in the 3D image data, a surface-based analysis component configured to create a flattened representation of the subject's brain using the acquire 3D image data and the subject-specific anatomical structures in the 3D image data, a model generation component configured to create a subject-specific model for electrical dynamics based on the flattened representation of the subject's brain, and a simulation component configured to calculate electrical wave propagation from an initial spreading point using the subject-specific model for electrical dynamics. In some embodiments, the modeling computing system may include one or more graphical processing units (GPUs) configured to parallelize execution of operations corresponding to these components.

In some embodiments, the system further includes a display configured to present a visualization of the electrical wave propagation from the initial spreading point. In one embodiment, this display presents a graphical user interface which allows user interaction with the visualization of the electrical wave propagation from the initial spreading point.

In some embodiments, the aforementioned system further includes an electrical sensing data acquisition device which is configured to acquire electrical sensing data representative of the subject's brain. This electrical sensing data acquisition device may be, for example, an EEG and/or an ECoG acquisition device. The model generation component may then be further configured to create an initial version of the subject-specific model for electrical dynamics based on the 3D image data and the subject-specific anatomical structures; and refine that initial version using the electrical sensing data.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, the drawings show embodiments that are presently preferred, it being understood, however, that the invention is not limited to the specific instrumentalities disclosed. Included in the drawings are the following Figures.

DETAILED DESCRIPTION

The present invention relates generally to methods, systems, and apparatuses for performing a subject-specific assessment of neurological disorder using imaging data. Briefly, in various embodiments described in greater detail below, a Lattice Boltzmann method based approach for fast computational modeling is combined with image understanding, segmentation and white matter tractography techniques for identifying subject-specific cortical structures to provide a complete solution for propagating brain waves. The disclosed methods, systems, and apparatuses provide an efficient technique that is suitable for clinical use and may be used, for example, in the diagnosis or treatment of Cortical Spreading Depression (CSD) and other neurological disorders. Some example applications for a personalized model are migraines with aura and epilepsy, as spreading depression has been closely associated with these conditions.

Figure 1:
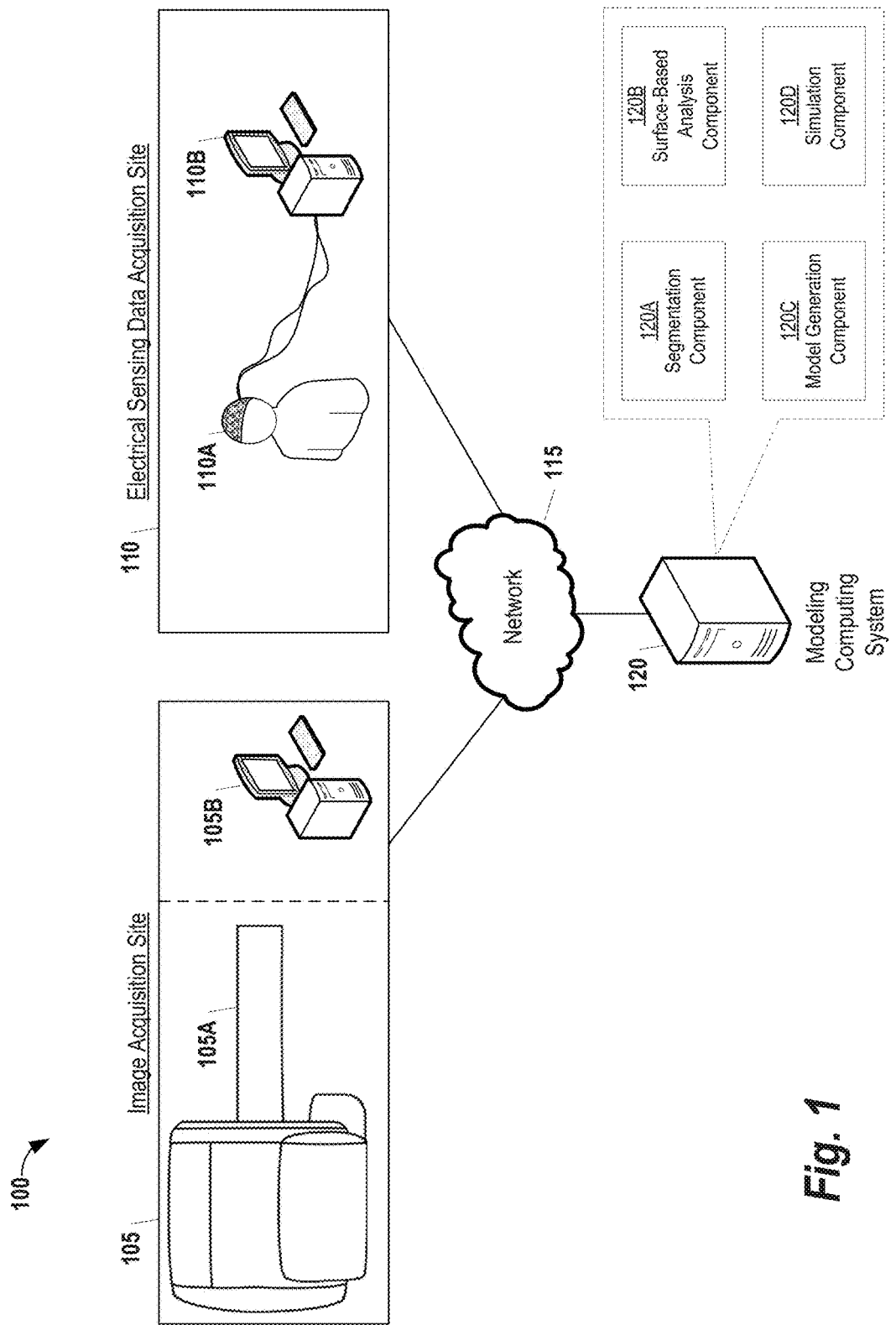
FIG. 1 provides a system for performing a subject-specific assessment of neurological disorders, according to some embodiments.

FIG. 1 provides a system 100 for performing a subject-specific assessment of neurological disorders, according to some embodiments. Briefly, an Imaging Device 105A at an Image Acquisition Site 105 is used to acquire data representative of a subject's brain. An Imaging Processing Computer 105B reconstructs an image of the subject's brain based on this data and makes it available over a Network 115. This Network 115 may be any network known in the art including, without limitation, the Internet or a facility intranet. The Modeling Computing System 120 then uses the brain image to generate a personalized model of electrical propagation for the individual. In some embodiments, data from an Electrical Sensing Data Acquisition Site 110 is used to further personalize the model for the subject. It should be noted that the configuration of sites and devices shown in FIG. 1 is merely one example of how such items may be organized. In other embodiments, one or more various devices shown in the FIG. 1 may be co-located at a single site. Additionally, various devices may be combined into a single unit in some embodiments.

At an Image Acquisition Site 105, one or more 3D brain images are acquired using an Imaging Device 105A. In the example of FIG. 1, an MRI device is shown. As is generally understood in the art, structural MRI (sMRI) provides information to qualitatively and quantitatively describe the shape, size, and integrity of gray and white matter structures in the brain. Many sMRI scans are volumetric, meaning that measurements can be made of specific brain structures to calculate volumes of tissue. It should be noted that the MRI is one example of an imaging modality that may be applied. In other embodiments, other imaging modalities capable of producing 3D images may be used.

Modeling Computing System 120 develops a subject-specific model for electrical dynamics based on the image data received from the Image Acquisition Site 105. For example, in some embodiments, the Modeling Computing System 120 determines subject-specific cortical geometry and connectivity information based on the received image data. Then, this subject-specific cortical geometry is combined with a Lattice Boltzmann method (or a similar computational fluid dynamics method) to develop a model of electrical dynamics in the brain, able to solve the dynamics of CSD using state-of-the-art ionic models. Generation of this model is described in greater detail below with reference to FIG. 2. The model for the electrical dynamics could be applied in the study of CSD but also, in principle, to other conditions where the mechanism of interest is a spreading wave (such as epilepsy). Since brain function depends to some extent on the integrity of brain structure, measures that characterize the underlying tissue integrity also allow one to examine the impact of tissue loss or damage on functional signals. Furthermore, in some embodiments, structural MRI provides an anatomical reference for visualization of activation patterns and regions of interest to extract functional signal information. Once the model is generated, it may be used by the Modeling Computing System 120 to simulate electrical wave propagation across the subject's brain and facilitate the detection of one or more functional indicators related to neurological disorder. The term functional indicator, as used herein, refers to any measurable indicator of the severity or presence of some neurological disease state. Examples of functional indicators include, without limitation, electrocorticography (ECoG) and electroencephalography (EEG).

In the example of FIG. 1, the Modeling Computing System 120 includes four components related to model generation and execution. These components may be embodied, for example, in one or more software functions, classes, or libraries. A Segmentation Component 120A is configured to identify subject-specific anatomical structures in the 3D image data. The Surface-Based Analysis Component 120B is configured to create a flattened representation of the subject's brain using the acquired 3D image data and the subject-specific anatomical structures in the 3D image data. The Model Generation Component 120C is configured to create a subject-specific model for electrical dynamics based on the flattened representation of the subject's brain. Finally, the Simulation Component 120D is configured to calculate wave propagation from an initial spreading point using the subject-specific model for electrical dynamics. Additional components may be included in the Modeling Computing System 120. For example, in some embodiments, the Modeling Computing System 120 may include components for detecting certain functional indicators based on user input and the subject-specific model for electrical dynamics.

Figure 2:
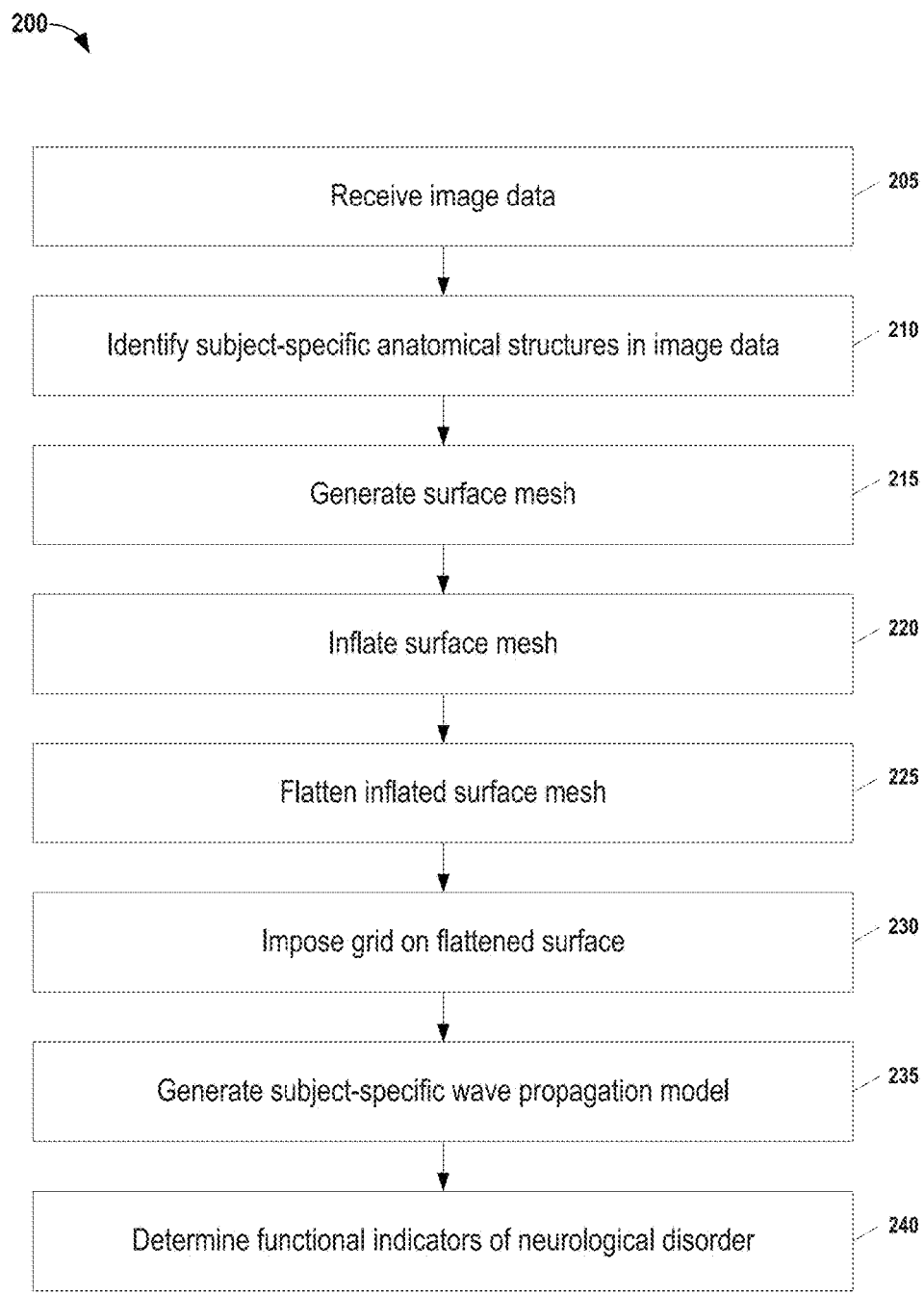
FIG. 2 illustrates a method for subject-specific brain electrophysiology simulation, according to some embodiments.

By taking into account electrical sensor measurements at various spatial locations, the subject-specific model for electrical dynamics developed by Modeling Computing System 120 may be further personalized for the individual. In FIG. 2, at Electrical Sensing Data Acquisition Site 110, an electroencephalography (EEG) Device 110A is used to acquire sensing data for the individual. This sensing data is then processed by Computer 110B and made available to the Modeling Server over the Network 115. Then, data from the model may be adjusted so that the propagation matches the EEG time series in various leads of the EEG Device 110A. It should be noted that EEG is only one example of sensing data that may be used with the techniques described herein. For example, in other embodiments, electrocorticography (ECoG) or similar techniques may be applied. In some embodiments, further biophysical refinement of the model for the electrical dynamics developed by Modeling Computing System 120 incorporates the effect of surrounding compartments in the form of conditions on the neurovascular and spatial coupling, for example, on the communication pathways between cortical and glial elements.

FIG. 2 illustrates a method 200 for subject-specific brain electrophysiology simulation, according to some embodiments. As illustrated in FIG. 2, at step 205, 3D medical image data is received from an imaging device such as Imaging Device 105A during a pre-operative process. The medical images may be received directly from a medical imaging device or the medical images may be received by loading stored medical images of a subject. In addition to medical image data, other subject-specific clinical data such as medical history information can also be received at step 205.

At step 210, subject-specific anatomical structures are identified based on the image data. These structures may be identified, in part, by segmenting the image data into a plurality of anatomical structures using one or more techniques generally known in the art. For example, in some embodiments, machine learning approaches may be used in the segmentation process. One example of a segmentation technique which uses marginal space learning (MSL) is described in U.S. patent application Ser. No. 12/558,736, filed Sep. 14, 2009 and entitled "Method and System for Segmentation of Brain Structures in 3D Magnetic Resonance Images," the entirety of which is incorporated herein by reference. Additionally, if diffusion information is available in the image data, one or more white matter tractography techniques known in the art may be applied to identify anatomical connections in the individual's brain. This diffusion information may be, for example, data representative of diffusion of fluid (e.g., water) through the subject's brain. This connection information may then be combined with other structural information determined via segmentation. One tractography technique is described in U.S. Pat. No. 7,881,878, filed Apr. 5, 2006 and entitled "Systems, devices, and methods for diffusion tractography," the entirety of which is incorporated herein by reference.

At step 215, a surface-based analysis (SBA) process is performed using the image data and the segmented anatomical structures to yield a surface mesh representing the cerebral cortex. Techniques for generating such a surface mesh are generally known in the art. In some embodiments, the SBA process may be implemented with conventional tools such as, without limitation, FreeSurfer, BrainVISA, Caret, or Brain Voyager. The surface mesh comprises a plurality of triangles joined together at vertex points. The coordinates of each of these vertex points may be derived, at least in part, based on the location of the segmented anatomical structures determined at step 210. In some embodiments, non-image subject data such as medical history or clinical application may also be used in determining the coordinates.

Next, at step 220, the surface mesh representing the cerebral cortex is inflated such that no area is hidden behind a fold. In some embodiments, as part of the inflation process performed at step 220, the inflated surface mesh is registered to a standard spherical atlas based on individual cortical folding patterns to ensure topological alignment of cortical areas. Various techniques known in the art may be used for performing the inflation process at step 220. For example, in some embodiments, an energy function is defined to smooth the surface while preserving the spatial positioning of the vertices. This function may then be minimized to yield the inflated shape. In some embodiments, one or more of the conventional SBA tools discussed above may be used to perform the inflation of the surface mesh. At step 225, the inflated mesh is flattened into one or more flat surfaces. A plurality of surface cuts are made to the inflated surface mesh-based on anatomical landmarks such as the subject-specific anatomical structures identified at step 225. These cuts may be made, for example, manually by a trained operator or through an automated cutting process. Once the desired cuts have been made, the resulting cut surface is spread out on a two-dimensional plane while minimizing distortion. Next, at step 230, a uniform Cartesian grid is imposed on the flattened surfaces created at step 225. The size of the Cartesian grid may vary in different embodiments and may be selected based on criteria such as, for example, the availability of computing resources. Alternatively, the algorithms could also operate on the mesh without flattening, for instance by embedding it in a higher-dimensional volume and using level sets to describe its surface.

Continuing with reference to FIG. 2, at step 235, a subject-specific model for electrical dynamics is generated based on the grid. In some embodiments, this subject-specific anatomical brain model uses one or more Lattice Boltzmann methods to constrain the spreading of a propagating wave across the subject's brain. As is generally understood in the art, Lattice Boltzmann methods are a powerful technique for accurate simulation of a large class of partial-differential equations. Some of the key strengths of Lattice Boltzmann methods are, i) local nature of the computational algorithm, which provides very high scalability on modern parallel computing architectures, ii) second-order accuracy in space, and iii) simplicity of implementation on a uniform Cartesian grid. Typically, in the context of wave propagation problems, the computation of data for a particular point in the domain requires information from many neighboring points. So, if one wants to compute how fast a wave is going at a particular point, one must determine how fast it arrived at all the different points in the neighborhood. Only then can the model advance to the next location, where the computation is repeated for the new location and neighbors. Lattice Boltzmann methods allow more of the computations to be performed with local information, minimizing the information required from neighbors. Then, a scattering component (a fast process) is used to communicate information to neighbors.

The dynamics of the different ionic species involved in such neurochemical disorders may be represented by means of partial differential equations. One example of such models, is the reaction-diffusion equation class of models at the tissue scale, where for each ion species (for instance $Na^+$, $K^+$, $Ca^{2+}$ etc.), an equation of the following form is specified:

$$\frac{\partial u}{\partial t} = \nabla \cdot D \nabla u + J(u, g)$$

$$\frac{dg}{dt} = f(g, u)$$

where, u is the instantaneous ionic concentration at each point, D is the diffusion constant for the ionic species and J(u, g) is the sum of all sources and sinks for this species. In this notation, the term g is used to denote hidden model variables, which have their own dynamics governed by the value of the ionic species and other model variables. This description is made complete by the specification of boundary and initial conditions for the ionic concentrations. It must be noted that other mathematical descriptions are possible, and this invention is not limited to the reaction-diffusion formulation.

From a computation perspective, the Lattice Boltzmann method is potentially resource intensive both in terms of memory and processing requirements. However, because the Lattice Boltzmann method generally needs only nearest neighbor information, the algorithm is an ideal candidate for parallel computing. Thus, in some embodiments, the model computations are performed in a parallel processing environment (see, e.g., FIG. 4). For example, in one embodiment, the grid is divided into spatially contiguous blocks along one axis. Then, multiple copies of the program for performing the model computations may be run simultaneously and independently, with each operating on its own block of data. Then, at the end of each iteration, the various processes may exchange information, as needed, to complete the iteration.

In some embodiments, given diffusion MRI data, deterministic or probabilistic white matter tractography techniques may be used to identify the fiber pathways between any two points in the mesh, yielding weights for the grid connecting all the grid nodes. This allows the modeling of non-uniform propagation dependent on the amount of white matter or coherent activation between any two points. In one embodiment, resting state functional MRI is used as an alternative to diffusion MRI for this purpose.

In some embodiments, the model for the electrical dynamics determined at step 235 may be further refined by model for the electrical dynamics by taking into account sensor measurements at various spatial locations, taken over time. For example, as discussed above with reference to the Electrical Sensing Data Acquisition Site 110 in FIG. 1, in some embodiments, a sensing technique such as EEG or ECoG may be used to gather the relevant measurements. Then, the subject-specific model for electrical dynamics is adjusted so that the propagation matches the sensing data time series in various leads. For example, the subject-specific model for electrical dynamics may be refined in an iterative loop until the data predicted by the model matches the real data produced by the sensing technique. Then, the constants and parameters of the subject-specific model for electrical dynamics may be set accordingly. Additionally in some embodiments, the model is further refined by incorporating the effect of surrounding compartments in the form of conditions on the neurovascular and spatial coupling (e.g., on the communication pathways between cortical and glial elements).

Returning to FIG. 2, once the model has been generated, at step 240 it is used to determine one or more functional indicators of neurological disorder. These functional indictors may then be used as guidance for further therapies. For example, in some embodiments, the model for the electrical dynamics generated using the techniques described herein may be used to make predictions about therapeutic efficacy of pharmacological treatments, given knowledge of how those treatments would affect parameters of CSD propagation (electrophysiology, blood flow, etc.) Beyond pharmacology, the model for the electrical dynamics may also be applied for Transcranial Magnetic Stimulation (TMS) treatments. TMS delivers a fluctuating magnetic field from the scalp surface to induce current in the subjacent cortex and has been shown to be effective as an acute treatment for migraine with aura. In this case, the model for the electrical dynamics may be used, for example, to test the effect of TMS at blocking CSD when administered in different head locations.

In epilepsy research, computational models have already played an important role in understanding the effects of different ions on the frequency of seizure events. Using the techniques described herein, the availability of fast models could enable the identification of new therapies. Another possible application would be the precise identification of the location of epileptogenic zones, albeit with a model of wave discharges rather than CSD. This is currently done by using implanted ECoG electrodes, an invasive procedure. There is already work towards replacing this with a combination of scalp EEG and structural MRI in some conventional systems; however this could be improved by the use of a more refined model for the electrical dynamics, especially if it also took into account diffusion MRI information. Much as with migraine, a personalized model could conceivably be used to study the effect of, or customize both pharmacological and TMS interventions.

In some embodiments, the subject-specific model for electrical dynamics is used to provide detailed visualizations of brain electrical activity. For example, videos may be developed showing wave propagation for display on a computing device. These videos may then be presented on a computing device (e.g., desktop computer monitor, smartphone, tablet, etc.) In this way, the information may be readily accessible in the clinical environment. Additionally, in some embodiments, the visualizations may allow for interactive exploration. In some cases, this visualization may entail operations such as rotation, zooming, etc., which allow the user to view different perspectives of the displayed data. In other embodiments, the interactive visualizations may be dynamic in nature and allow the user to directly change parameters of the underlying model to view the effect on the visualization. Visualizations may also utilize virtual reality and/or augmented reality technologies generally known in the art to further enhance the interactivity of the data.

Figure 3:
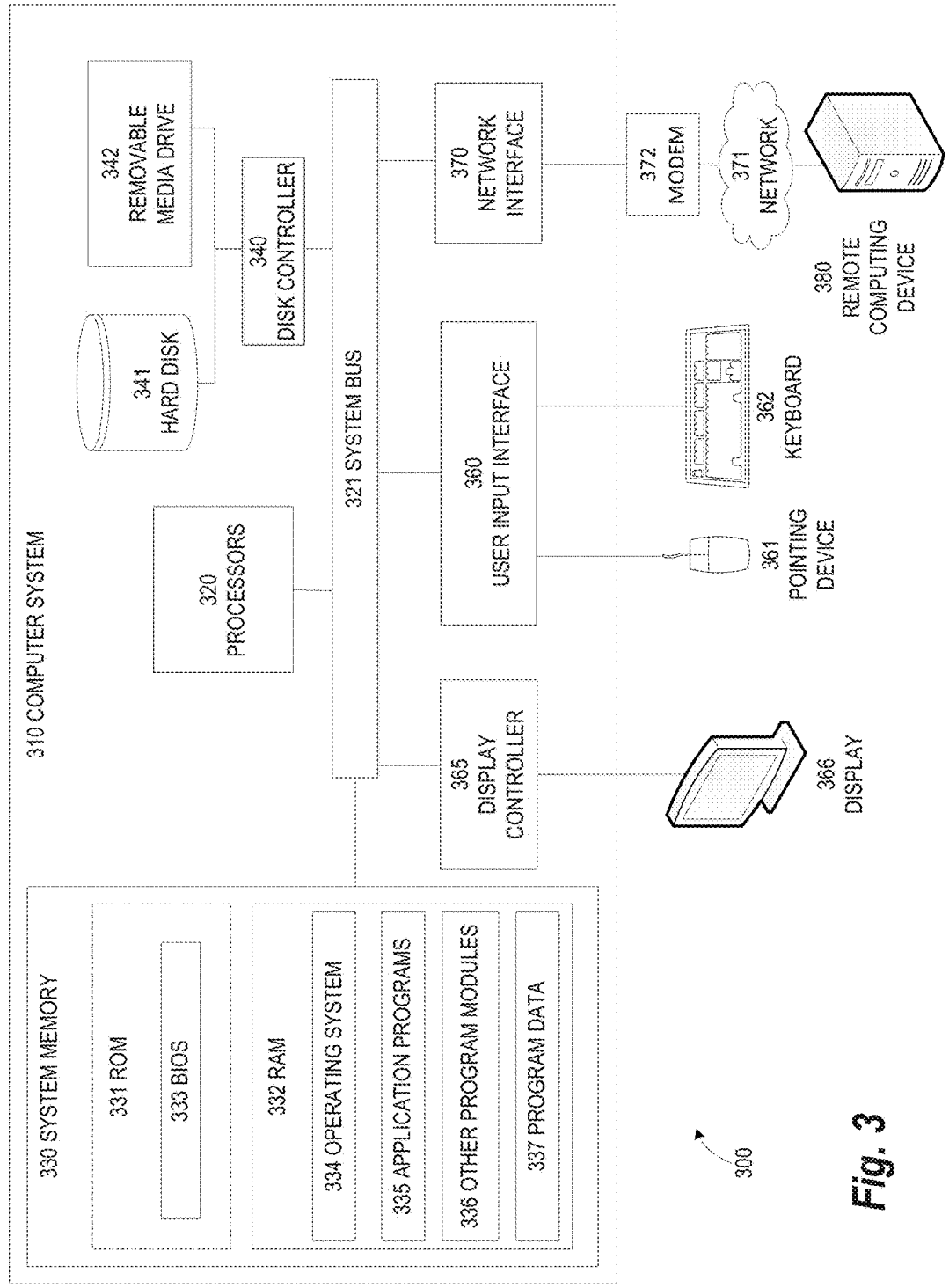
FIG. 3 illustrates an exemplary computing environment within which embodiments of the invention may be implemented.

FIG. 3 illustrates an exemplary computing environment 300 within which embodiments of the invention may be implemented. For example, this computing environment 300 may be used to implement the Modeling Computing System 120 shown in FIG. 1, as well as the method 200 described in FIG. 2. The computing environment 300 may include computer system 310, which is one example of a computing system upon which embodiments of the invention may be implemented. Computers and computing environments, such as computer system 310 and computing environment 300, are known to those of skill in the art and thus are described briefly here.

As shown in FIG. 3, the computer system 310 may include a communication mechanism such as a bus 321 or other communication mechanism for communicating information within the computer system 310. The computer system 310 further includes one or more processors 320 coupled with the bus 321 for processing the information. The processors 320 may include one or more central processing units (CPUs), graphical processing units (GPUs), or any other processor known in the art.

The computer system 310 also includes a system memory 330 coupled to the bus 321 for storing information and instructions to be executed by processors 320. The system memory 330 may include computer readable storage media in the form of volatile and/or nonvolatile memory, such as read only memory (ROM) 331 and/or random access memory (RAM) 332. The system memory RAM 332 may include other dynamic storage device(s) (e.g., dynamic RAM, static RAM, and synchronous DRAM). The system memory ROM 331 may include other static storage device(s) (e.g., programmable ROM, erasable PROM, and electrically erasable PROM). In addition, the system memory 330 may be used for storing temporary variables or other intermediate information during the execution of instructions by the processors 320. A basic input/output system 333 (BIOS) containing the basic routines that help to transfer information between elements within computer system 310, such as during start-up, may be stored in ROM 331. RAM 332 may contain data and/or program modules that are immediately accessible to and/or presently being operated on by the processors 320. System memory 330 may additionally include, for example, operating system 334, application programs 335, other program modules 336 and program data 337.

The computer system 310 also includes a disk controller 340 coupled to the bus 321 to control one or more storage devices for storing information and instructions, such as a hard disk 341 and a removable media drive 342 (e.g., floppy disk drive, compact disc drive, tape drive, and/or solid state drive). The storage devices may be added to the computer system 310 using an appropriate device interface (e.g., a small computer system interface (SCSI), integrated device electronics (IDE), Universal Serial Bus (USB), or FireWire).

The computer system 310 may also include a display controller 365 coupled to the bus 321 to control a display 366, such as a cathode ray tube (CRT) or liquid crystal display (LCD), for displaying information to a computer user. The computer system includes an input interface 360 and one or more input devices, such as a keyboard 362 and a pointing device 361, for interacting with a computer user and providing information to the processor 320. The pointing device 361, for example, may be a mouse, a trackball, or a pointing stick for communicating direction information and command selections to the processor 320 and for controlling cursor movement on the display 366. The display 366 may provide a touch screen interface which allows input to supplement or replace the communication of direction information and command selections by the pointing device 361.

The computer system 310 may perform a portion or all of the processing steps of embodiments of the invention in response to the processors 320 executing one or more sequences of one or more instructions contained in a memory, such as the system memory 330. Such instructions may be read into the system memory 330 from another computer readable medium, such as a hard disk 341 or a removable media drive 342. The hard disk 341 may contain one or more data stores and data files used by embodiments of the present invention. Data store contents and data files may be encrypted to improve security. The processors 320 may also be employed in a multi-processing arrangement to execute the one or more sequences of instructions contained in system memory 330. In alternative embodiments, hard-wired circuitry may be used in place of or in combination with software instructions. Thus, embodiments are not limited to any specific combination of hardware circuitry and software.

As stated above, the computer system 310 may include at least one computer readable medium or memory for holding instructions programmed according embodiments of the invention and for containing data structures, tables, records, or other data described herein. The term "computer readable medium" as used herein refers to any medium that participates in providing instructions to the processor 320 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 341 or removable media drive 342. Non-limiting examples of volatile media include dynamic memory, such as system memory 330. Non-limiting examples of transmission media include coaxial cables, copper wire, and fiber optics, including the wires that make up the bus 321. Transmission media may also take the form of acoustic or light waves, such as those generated during radio wave and infrared data communications.

The computing environment 300 may further include the computer system 310 operating in a networked environment using logical connections to one or more remote computers, such as remote computer 380. Remote computer 380 may be a personal computer (laptop or desktop), a mobile device, a server, a router, a network PC, a peer device or other common network node, and typically includes many or all of the elements described above relative to computer system 310. When used in a networking environment, computer system 310 may include modem 372 for establishing communications over a network 371, such as the Internet. Modem 372 may be connected to bus 321 via user network interface 370, or via another appropriate mechanism.

Network 371 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 310 and other computers (e.g., remote computer 380). The network 371 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 371.

Figure 4:
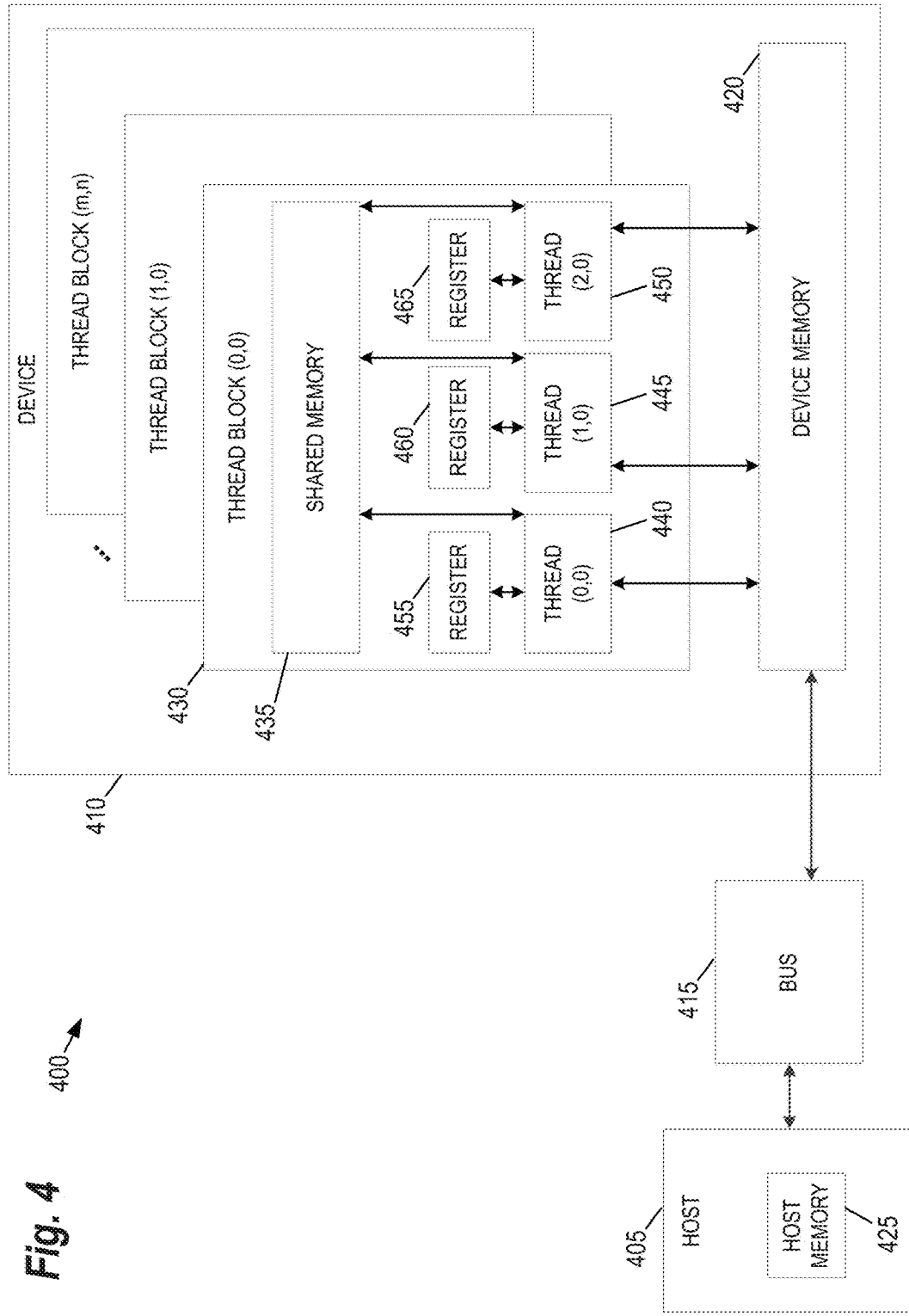
FIG. 4 provides an illustration of the parallel processing platform that may be utilized to accelerate computation and execution of the subject-specific model for electrical dynamics, according to some embodiments.

FIG. 4 provides an illustration of the parallel processing platform 400 that may be utilized to accelerate computation and execution of the subject-specific model for electrical dynamics, according to some embodiments. For example, the parallel processing platform 400 may be included in Modeling Computing System 120 shown in FIG. 1 or, alternatively, the platform 400 may be connected to the Modeling Computing System 120 in a manner that allows the Modeling Computing System 120 to off-load computations to the platform 400. The parallel processing platform 400 may be used, for example, for implementations of the present invention where NVIDIA™ CUDA (or a similar parallel computing platform) is used. The architecture illustrated in FIG. 4 includes a host computing unit ("host") 405 and a GPU device ("device") 410 connected via a bus 415 (e.g., a PCIe bus). The host 405 includes the CPU (not shown in FIG. 4) and host memory 425 accessible to the CPU. The graphical processing device 410 includes the GPU and its associated device memory 420, referred to herein as device memory. The device memory 420 may include various types of memory, each optimized for different memory usages. For example, in some embodiments, the graphical processing device memory includes global memory, constant memory, and texture memory. Parallel portions of an application may be executed on the platform 400 as "device kernels" or simply "kernels." A kernel comprises parameterized code configured to perform a particular function. The parallel computing platform is configured to execute these kernels in an optimal manner across the platform 400 based on parameters, settings, and other selections provided by the user. Additionally, in some embodiments, the parallel computing platform may include additional functionality to allow for automatic processing of kernels in an optimal manner with minimal input provided by the user.

The processing required for each kernel is performed by a grid of thread blocks. Using concurrent kernel execution, streams, and synchronization with lightweight events, the platform 400 of FIG. 4 (or similar architectures) may be used to parallelize various operations involved with solving the computational model. The graphical processing device 410 includes one or more thread blocks 430 which represent the computation unit of the graphical processing device. The term thread block refers to a group of threads that can cooperate via shared memory and synchronize their execution to coordinate memory accesses. For example, in FIG. 4, threads 440, 445 and 450 operate in thread block 430 and access shared memory 435. Depending on the parallel computing platform used, thread blocks may be organized in a grid structure. A computation or series of computations may then be mapped onto this grid. For example, in embodiments utilizing CUDA, computations may be mapped on one-, two-, or three-dimensional grids. Each grid contains multiple thread blocks, and each thread block contains multiple threads. For example, in FIG. 4, the thread blocks 430 are organized in a two dimensional grid structure with m+1 rows and n+1 columns. Generally, threads in different thread blocks of the same grid cannot communicate or synchronize with each other. However, thread blocks in the same grid can run on the same multiprocessor within the GPU at the same time. The number of threads in each thread block may be limited by hardware or software constraints.

Continuing with reference to FIG. 4, registers 455, 460, and 465 represent the fast memory available to thread block 430. Each register is only accessible by a single thread. Thus, for example, register 455 may only be accessed by thread 440. Conversely, shared memory is allocated per thread block, so all threads in the block have access to the same shared memory. Thus, shared memory 435 is designed to be accessed, in parallel, by each thread 440, 445, and 450 in thread block 430. Threads can access data in shared memory 435 loaded from device memory 420 by other threads within the same thread block (e.g., thread block 430). The device memory 420 is accessed by all blocks of the grid and may be implemented using, for example, Dynamic Random-Access Memory (DRAM).

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112(f), unless the element is expressly recited using the phrase "means for."

The invention claimed is:

1. A method for subject-specific assessment of neurological disorders, the method comprising:
   receiving 3D image data representative of a subject's brain, wherein the 3D image data comprises (i) structural data representative of structures in the subject's brain and (ii) diffusion data representative of diffusion of fluid through the subject's brain;
   identifying subject-specific anatomical structures using the structural data;
   identifying a plurality of subject-specific anatomical connections in the subject's brain using the diffusion data;
   using the 3D image data to perform surface based analysis of the subject's brain, yielding a flattened representation of the subject's brain;
   imposing a grid on the flattened representation of the subject's brain using the subject-specific anatomical structures, wherein the grid comprises a plurality of grid nodes and a plurality of edges connecting the grid nodes;
   weighing the edges of the grid based on the subject-specific anatomical connections, thereby yielding a weighted grid;
   creating a subject-specific model for electrical dynamics based on the weighted grid, wherein the subject-specific model for electrical dynamics utilizes one or more Lattice Boltzmann methods;
   computing, by a parallel processing platform, one or more functional indicators of neurological disorder using the subject-specific model for electrical dynamics, wherein the Lattice Boltzmann methods are used to parallelize at least a portion of computations performed by the subject-specific model across a plurality of processors included in the parallel processing platform.

2. The method of claim 1, wherein the subject-specific anatomical structures are identified by a process comprising:
   applying a machine learning process to segment the subject's brain into a plurality of brain segments,
   wherein the subject-specific anatomical structures comprises the plurality of brain segments.

3. The method of claim 1, wherein the surface based analysis comprises:
   generating a surface mesh of the subject's brain;
   inflating the surface mesh to yield an inflated mesh;
   flattening the inflated mesh to yield the flattened representation of the subject's brain.

4. The method of claim 1, further comprising:
   receiving electrical sensing data representative of the subject's brain,
   wherein the subject-specific model for electrical dynamics is created using the electrical sensing data.

5. The method of claim 4, wherein the subject-specific model for electrical dynamics is created by a process comprising:
   creating an initial version of the subject-specific model for electrical dynamics based on the 3D image data and the subject-specific anatomical structures; and
   refining the initial version of the subject-specific model for electrical dynamics using the electrical sensing data to yield the subject-specific model for electrical dynamics.

6. The method of claim 4, wherein the electrical sensing data comprises electroencephalography (EEG) data.

7. The method of claim 4, wherein the electrical sensing data comprises electrocorticography (ECoG) data.

8. A method for subject-specific assessment of neurological disorders, the method comprising:
   receiving 3D image data representative of a subject's brain, wherein the 3D image data comprises (i) structural data representative of structures in the subject's brain and (ii) diffusion data representative of diffusion of fluid through the subject's brain;
   identifying subject-specific anatomical structures in the 3D image data;
   identifying a plurality of subject-specific anatomical connections in the subject's brain using the diffusion data;
   generating a surface mesh of the subject's brain based on the 3D image data;
   applying an inflation process to the surface mesh to yield an inflated mesh;
   applying a flattening process to the inflated mesh to yield the flattened representation of the subject's brain;
   imposing a grid on the flattened representation of the subject's brain using the subject-specific anatomical structures, wherein the grid comprises a plurality of grid nodes and a plurality of edges connecting the grid nodes;
   weighing the edges of the grid based on the subject-specific anatomical connections, thereby yielding a weighted grid;

generating a subject-specific model for electrical dynamics using the weighted grid, wherein the subject-specific model for electrical dynamics utilizes one or more Lattice Boltzmann methods;
dividing the grid into a plurality of blocks;
using a parallel computing platform to compute one or more functional indicators of neurological disorder by executing multiple copies of the subject-specific model for electrical dynamics in parallel, wherein each respective copy corresponds to one of the plurality of blocks.

9. The method of claim 8, further comprising:
receiving electrical sensing data representative of the subject's brain,
generating an initial version of the subject-specific model for electrical dynamics based on the 3D image data and the subject-specific anatomical structures; and
refining the initial version of the subject-specific model for electrical dynamics using the electrical sensing data to yield the subject-specific model for electrical dynamics.

10. The method of claim 8, wherein the subject-specific anatomical structures are identified by a process comprising:
applying a machine learning process to segment the subject's brain into a plurality of brain segments,
identifying diffusion data included in the 3D image data, the diffusion data information representative of diffusion of fluid through the subject's brain; and
identifying a plurality of anatomical connections in the subject's brain using the diffusion data,
wherein the subject-specific anatomical structures further comprise the plurality of brain segments and the plurality of anatomical connections.

11. A system for calculating electrical wave propagation across a subject's brain, the system comprising:
one or more imaging devices configured to acquire 3D image data representative of a subject's brain, wherein the 3D image data comprises (i) structural data representative of structures in the subject's brain and (ii) diffusion data representative of diffusion of fluid through the subject's brain;
a modeling computing system operably coupled to the imaging devices and configured to use a plurality of processors to simulate electrical dynamics across the subject's brain, the processors performing the modeling computing system comprising system memory storing instructions, which instructions are configures to perform a method comprising:
identifying subject-specific anatomical structures in the 3D image data,
identifying a plurality of subject-specific anatomical connections in the subject's brain using the diffusion data,
using the 3D image data to perform surface based analysis of the subject's brain, yielding a flattened representation of the subject's brain,
imposing a grid on the flattened representation of the subject's brain using the subject-specific anatomical structures and the subject-specific anatomical connections, wherein the grid comprises a plurality of grid nodes and a plurality of edges connecting the grid nodes,
weighing the edges of the grid based on the subject-specific anatomical connections, thereby yielding a weighted grid;
creating a subject-specific model for electrical dynamics based on the weighted grid, wherein the subject-specific model for electrical dynamics utilizes one or more Lattice Boltzmann methods, and
calculating electrical wave propagation from an initial spreading point using the subject-specific model for electrical dynamics, wherein the Lattice Boltzmann methods are used to parallelize at least a portion of computations performed by the subject-specific model across the processors.

12. The system of claim 11, wherein at least one of the imaging devices is a Magnetic Resonance Imaging (MM) device.

13. The system of claim 11, further comprising:
an electrical sensing data acquisition device configured to acquire electrical sensing data representative of the subject's brain.

14. The system of claim 13, wherein the processors are further configured to:
create an initial version of the subject-specific model for electrical dynamics based on the 3D image data and the subject-specific anatomical structures; and
refine the initial version of the subject-specific model for electrical dynamics using the electrical sensing data.

15. The system of claim 13, wherein the electrical sensing data acquisition device comprises an electroencephalography (EEG) acquisition device.

16. The system of claim 13, wherein the electrical sensing data acquisition device comprises an electrocorticography (ECoG) acquisition device.

17. The system of claim 13, wherein the modeling computing system comprises one or more graphical processing units (GPUs) configured to parallelize execution of operations corresponding to the simulation of electrical dynamics across the subject's brain.

18. The system of claim 11, further comprising:
a display configured to present a visualization of the electrical wave propagation from the initial spreading point.

19. The system of claim 18, wherein the display is further configured to present a graphical user interface which allows user interaction with the visualization of the electrical wave propagation from the initial spreading point.

* * * * *